(12) United States Patent
Hell

(10) Patent No.: US 9,291,562 B2
(45) Date of Patent: Mar. 22, 2016

(54) METHOD AND APPARATUS FOR TRACKING A PARTICLE, PARTICULARLY A SINGLE MOLECULE, IN A SAMPLE

(71) Applicant: Max-Planck-Gesellschaft zur Foerderung der Wissenschaften e.V., Munich (DE)

(72) Inventor: Stefan W. Hell, Goettingen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 241 days.

(21) Appl. No.: 14/050,583

(22) Filed: Oct. 10, 2013

(65) Prior Publication Data
US 2014/0042340 A1 Feb. 13, 2014

Related U.S. Application Data

(63) Continuation-in-part of application No. PCT/EP2012/072375, filed on Nov. 12, 2012.

(30) Foreign Application Priority Data

Nov. 15, 2011 (DE) .......................... 10 2011 055 367

(51) Int. Cl.
*G01N 21/64* (2006.01)
*G01N 15/14* (2006.01)

(52) U.S. Cl.
CPC ............ *G01N 21/64* (2013.01); *G01N 15/1434* (2013.01); *G01N 21/645* (2013.01); *G01N 21/6428* (2013.01); *G01N 21/6458* (2013.01); *G01N 21/6486* (2013.01)

(58) Field of Classification Search
CPC .............. G01N 21/64; G01N 21/6486; G01N 21/6458; G01N 21/6428
See application file for complete search history.

(56) References Cited

U.S. PATENT DOCUMENTS

| 3,960,449 A | 6/1976 | Carleton et al. |
| 3,999,855 A | 12/1976 | Hirschfeld |

(Continued)

FOREIGN PATENT DOCUMENTS

| CN | 101877130 A | 2/2010 |
| CN | 101655460 A | 11/2010 |

(Continued)

OTHER PUBLICATIONS

Klar et al., "Fluorescence Microscopy with Diffraction Resolution Barrier Broken by Stimulated Emission," PNAS vol. 97, No. 15, pp. 8206-8210, (Jul. 18, 2000).
Westphal et al., "Nanoscale Resolution in the Focal Plane of an Optical Microscope,", Phys. Rev. Letters, 94 (Apr. 15, 2005), pp. 143903-1 to 143903-4.
Donnert et al., "Macromolecular-scale Resolution in Biological Fluorescence Microscopy," PNAS, vol. 103, No. 31, pp. 11440-11445 (Aug. 1, 2006).

(Continued)

*Primary Examiner* — Christine Sung
(74) *Attorney, Agent, or Firm* — Thomas | Horstemeyer, LLP

(57) ABSTRACT

For the purpose of tracking a movement of a particle in a sample, the particle is driven by light to emit photons, and the photons emitted by the particle are detected. The light applied to the sample features a light intensity distribution with a spatially limited minimum. The particle is tracked with the minimum of the light intensity distribution by moving the light intensity distribution with respect to the sample such that a rate of photons emitted by the particle remains minimal, and by taking an actual position of the minimum of the light intensity distribution in the sample as an actual position of the particle in the sample.

50 Claims, 6 Drawing Sheets

(56) References Cited

U.S. PATENT DOCUMENTS

| | | | |
|---|---|---|---|
| 5,793,478 | A | 8/1998 | Rader et al. |
| 6,498,645 | B1 | 12/2002 | Knapp et al. |
| 6,587,809 | B2 | 7/2003 | Major |
| 7,002,682 | B2 | 2/2006 | Girvin |
| 7,800,750 | B2 | 9/2010 | Bustamante et al. |
| 2003/0007894 | A1 | 1/2003 | Wang et al. |
| 2009/0015831 | A1 | 1/2009 | Yguerabide et al. |
| 2009/0242801 | A1* | 10/2009 | Engelhardt et al. ........ 250/459.1 |
| 2010/0140506 | A1 | 6/2010 | Eggeling et al. |
| 2010/0225913 | A1 | 9/2010 | Trainer |
| 2011/0222062 | A1 | 9/2011 | Martini et al. |
| 2012/0134682 | A1 | 5/2012 | Capron et al. |
| 2013/0294645 | A1* | 11/2013 | Sibarita ........................ 382/103 |
| 2014/0120627 | A1* | 5/2014 | Rubino et al. .................. 436/72 |
| 2014/0134608 | A1* | 5/2014 | Hanashi et al. .................. 435/5 |

FOREIGN PATENT DOCUMENTS

| | | |
|---|---|---|
| CN | 102063580 A | 5/2011 |
| DE | 25 46 952 A1 | 4/1976 |
| DE | 199 35 047 A1 | 2/2001 |
| DE | 100 53 747 A1 | 5/2002 |
| DE | 10 2007 033 737 A1 | 1/2009 |
| DE | 10 2009 019 013 A1 | 10/2010 |
| EP | 2 246 699 B1 | 4/2010 |
| WO | 02/40978 A2 | 5/2002 |

OTHER PUBLICATIONS

J. Keller et al., "Efficient fluorescence inhibition patterns for RESOLFT microscopy", Optics Express 3361, vol. 15, No. 6 (Mar. 19, 2007).

B. Harke et al., "Three-Dimensional Nanoscopy of Colloidal Crystals", NanoLetters, American Chemical Society, vol. 8, No. 5, pp. 1309-1313 (Jan. 1, 2008).

S.J. Sahl et al., "Fast molecular tracking maps nanoscale dynamics of plasma membrane lipids", PNAS, Apr. 13, 2010, vol. 107, No. 15, 6829-6834.

A. Schönle and S.W. Hell, "Fluorescence nanoscopy goes multicolor", Nature Biotechnology, vol. 25, No. 11, Nov. 2007, 1234-1235.

Huang et al., "Three-Dimensional Super-Resolution Imaging by Stochastic Optical Reconsitruction Microscopy", Science 319, 810 (2008).

Pavani et al., "Three-Dimensional, Single-Molecule Fluorescence Imaging Beyond the Diffraction Limit by Using a Double-Helic Point Spread Function," PNAS vol. 106, No. 9, pp. 2995-2999 (Mar. 3, 2009).

PCT Search Report in co-pending, related PCT application No. PCT/EP2012/072375, mailed Feb. 21, 2013.

Chinese Office Search Report (with English Translation) in co-pending, related Chinese Application No. 201280059918.5, mailed Oct. 10, 2015.

* cited by examiner

METHOD AND APPARATUS FOR TRACKING A PARTICLE, PARTICULARLY A SINGLE MOLECULE, IN A SAMPLE

CROSS REFERENCE TO RELATED APPLICATIONS

This application is a continuation-in-part (CIP) of International Application PCT/EP2012/072375 with an International Filing Date of Nov. 12, 2012 and claiming priority to German Patent Application No. 10 2011 055 367.3 entitled "Verfahren and Vorrichtung zum Verfolgen einer Bewegung eines Partikels, insbesondere eines einzelnen Moleküls, in einer Probe", filed on Nov. 15, 2011.

FIELD OF THE DISCLOSURE

The disclosure relates to a method of tracking a movement of a particle in a sample, the particle being driven to emit photons when subjected to light, and the photons emitted by the particle being detected. Further, the disclosure relates to an apparatus for performing such a method comprising a light source providing the light and a detector detecting the photons.

BACKGROUND OF THE DISCLOSURE

According to a known method of tracking a movement of a single molecule in a sample, the molecule is excited with light for emitting photons, and the photons emitted by the molecule are detected with a two-dimensional detector imaging the sample. The current position of the molecule is then determined from the spatial distribution of the photons detected by the detector. With an appropriate pixel density of the detector, a present position of the molecule can be determined from the spatial distribution of the photons at a spatial resolution or precision surpassing the diffraction limit. However, it is a precondition of tracking the particle at a spatial precision beyond the diffraction limit that a high number of photons is detected for each position of the molecule, i.e. before the molecule changes its position. This is due to the fact that a higher number of photons enhances the spatial precision achieved in determining the position of the molecule, only if this position remains unchanged for the whole period over which the higher number of photons are emitted by the molecule.

The spatial precision is given by the radius $\Delta r$ of a circle around a position of the molecule determined from the centre of intensity of a distribution of positions at which the photons emitted by the molecule are detected by a two-dimensional detector. The true position of the molecule is located within that circle. The radius $\Delta r$ is given by $$\Delta r = FWHM/N^{1/2} \quad (1)$$

and depends on the number N of detected photons and on the full width at half maximum FWHM of the diffraction pattern.

As the known method of tracking a movement of a single molecule requires a huge number N of photons for each position of the molecule in the sample, the molecule is seriously stressed which results in an increased risk of bleaching the molecule. In the process of bleaching, the molecule chemically changes such that no more photons are provided by the molecule after bleaching. Besides photochemical bleaching, it is also possible that a molecule which has been intensively and/or numerously excited to emit photons is transferred into a metastable dark state. From the metastable dark state the molecule may return after some time. In the metastable dark state, however, the molecule does not emit any photons required for continuously tracking the molecule.

Consequently, there are only some molecules, i.e. only some so-called fluorescent dyes or fluorophores, which are suited for use in the known method. Many fluorophores bleach too fast and hence their movement or the movement of a molecule marked with the fluorophore cannot be tracked for an extended period of time or a longer distance covered within the sample.

In the method described above, the position of the molecule is determined from the distribution of positions at which the photons emitted by the molecule are detected by a two-dimensional detector. This approach is called localization. Another approach for achieving a high resolution or precision in determining a spatial position of photon emitting molecules is so-called STED or RESOLFT fluorescence microscopy. Here, the spatial region in which the molecules in a sample are effectively excited to emit photons is reduced to a size smaller than the diffraction limit. Thus, the photons emitted from the sample can be attributed to this particular spatial region of reduced size independent from the position where the photons are detected and independent from the number of photons detected. In practice, the reduction of the spatial region of effectively exciting the molecules to emit photons is achieved by applying a focused excitation light beam which is superimposed with an interference pattern of one or more coherent beams of fluorescence inhibiting light. This interference pattern comprises a point of essentially zero intensity in the focal region of the excitation light beam. For high absolute intensities of the beams of fluorescence inhibiting light, the intensity of the fluorescence inhibiting light exceeds a saturation intensity $I_S$ anywhere but at the point of essentially zero intensity such that the emission of photons by the molecules in the sample is inhibited essentially anywhere but at the point of essentially zero intensity. The achieved spatial resolution or precision is given by $$\Delta r = \lambda (n \sin \alpha (1 + I/I_S)^{1/2}) \quad (2),$$

wherein I is the maximal intensity of the interference pattern in the sample.

In STED fluorescence microscopy the inhibition of fluorescence is achieved by stimulated emission. In case of RESOLFT fluorescence microscopy the inhibition of fluorescence is achieved by temporarily transferring the molecules into a conformational or other type of state in which the molecules are not capable to fluoresce. Since in STED fluorescence microscopy high absolute intensities of the fluorescence inhibiting light are required, the risk of bleaching the fluorophores is relatively high. For RESOLFT fluorescence microscopy, relatively low intensities of the fluorescence inhibiting light are sufficient. However, this approach can only be applied with special fluorophores that can be switched into a conformational or other type of state in which the fluorophores are not capable to fluoresce.

In general, approaches like a STED or RESOLFT fluorescence microscopy would be suited for tracking a movement of a particle in a sample, in that the particle is tracked with the region of spatially reduced size where the particle is effectively excited to emit fluorescence light. In this case, the criterion for the particle being in the region of spatially reduced size would be a maximum rate of photons emitted by the tracked particle. Although less photons would be required for tracking according to this approach than for continuous localization of the particle, the number of particles and markers which are suited for tracking a movement over longer distances could not be significantly increased. Besides, in STED and RESOLFT fluorescence microscopy, different light beams have to be applied for providing the excitation light and the light for inhibiting fluorescence. Typically, this requires additional effort since the different light beams have different wavelengths and since the different light beams have to be carefully aligned spatially.

From DE 25 46 952 A1 it is known that an optical system based on so-called attenuated total reflectance may be applied to track movements of particles in a sample. According to DE 25 46 952 A1 the sample is subjected to light driving the particles to emit photons. Since the intensity distribution of the light illuminating the sample is not homogeneous but spatially modulated, a movement of the particle results in a respective fluctuation of the number of emitted photons. Thus, considering the modulation of the intensity distribution, the movement of the particle can be concluded from the detected fluctuation of the emitted photons, i.e. the modulation of a detector signal. However, a movement of a particle moving along a path of constant light intensity cannot be tracked. Further, a particle never or only rarely subjected to the light during its movement cannot be tracked at all. Thus, it is essential for tracking the movements of particles in a sample with the optical system known from DE 25 46 952 A1 that the particles are frequently subjected to the light. Hence, the risk of bleaching the particles or markers marking the particles is not effectively diminished but has to be accepted.

There still is a need of a method of and an apparatus for tracking a movement of a particle in a sample in which the risk of bleaching the particle or the marker marking the particle remains small, even if the movement of the particle is tracked for a longer period of time or over a longer distance.

SUMMARY

The present disclosure relates to a method of tracking a movement of a particle in a sample. The method starts with providing light; selecting the particle from a group of particles which are driven to emit photons when subjected to the light. The light is formed to provide a light intensity distribution comprising a spatially limited minimum. The light intensity distribution is applied to the sample such that the particle is located in the spatially limited minimum of the light intensity distribution. The photons emitted by the particle are detected. The movement of the particle is tracked with the spatially limited minimum of the light intensity distribution in that the light intensity distribution is moved with respect to the sample such that a rate of the photons emitted by the particle remains minimal, and in that an actual position of the spatially limited minimum of the light intensity distribution in the sample is taken as an actual position of the particle in the sample.

The present disclosure also relates to a method of imaging a sample. This method comprises the steps of (i) providing light of a first composition; (ii) selecting a particle from a first group of particles which are driven to emit photons when subjected to the light of the first composition; (iii) forming the light of the first composition to provide a light intensity distribution comprising a spatially limited minimum; (iv) applying the light intensity distribution to the sample such that the particle is located in the spatially limited minimum of the light intensity distribution; (v) detecting the photons emitted by the particle; tracking the movement of the particle with the spatially limited minimum of the light intensity distribution by (vi) moving the light intensity distribution with respect to the sample such that a rate of the photons emitted by the particle remains minimal, and (vii) taking an actual position of the spatially limited minimum of the light intensity distribution in the sample as an actual position of the particle in the sample; (viii) for each of a plurality of parts of the sample, determining a dwell time of the particle; and (ix) mapping a distribution of the dwell times over the sample.

Further, the present disclosure relates to an apparatus for tracking a movement of a particle in a sample. The apparatus comprises a light source configured to provide light for driving the particle to emit photons, beam shaping means configured to apply the light to the sample with an intensity distribution comprising a spatially limited minimum, a detector configured to detect the photons emitted out of a volume including the spatially limited minimum of the light intensity distribution and to provide a signal indicating a rate of the photons detected, and beam deflecting means configured to move the intensity distribution with respect to the sample and to be controlled based on the signal of the detector such that a rate of the photons detected by the detector remains minimal.

Advantageous further developments of the disclosure result from the claims, the description and the drawings. The advantages of features and of combinations of a plurality of features mentioned in this description only serve as examples and may be used alternatively or cumulatively without the necessity of embodiments according to the disclosure having to achieve these advantages. Without altering the scope of protection as defined by the enclosed claims, the following applies with respect to the disclosure of the original application and the patent: further features may be taken from the drawings, in particular from the illustrated designs and the dimensions of a plurality of components with respect to one another as well as from their relative arrangement and their operative connection. The combination of features of different embodiments of the disclosure or of features of different claims independent from the chosen references of the claims is also possible, and it is motivated herewith. This also relates to features which are illustrated in separate drawings, or which are mentioned when describing them. These features may also be combined with features of different claims. Furthermore, it is possible that further embodiments of the disclosure do not have all the features mentioned in the claims. They may even not have all the features mentioned in the independent claims.

BRIEF DESCRIPTION OF THE DRAWINGS

In the following, the disclosure is further explained and described with reference to preferred exemplary embodiments illustrated in the drawings.

DETAILED DESCRIPTION

Figure 1:
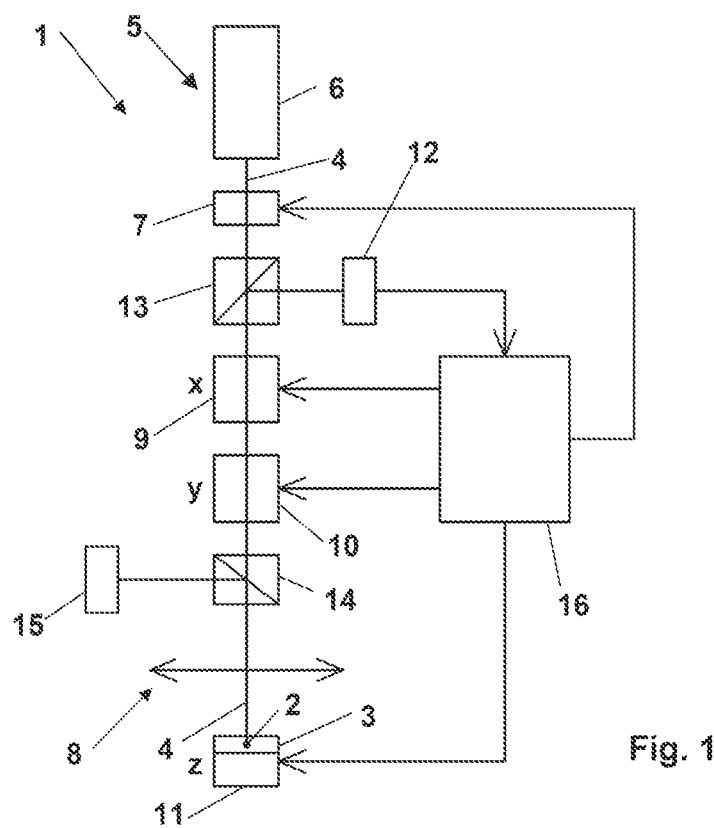
FIG. 1 illustrates an exemplary embodiment of an apparatus according to the present disclosure for performing an embodiment of a method according to the present disclosure, the apparatus comprising one light source, a point detector and a camera.

The particle whose movement in the sample is tracked according to the present disclosure may be a single molecule, a group of molecules moving together, a complex, a quantum dot, a reflecting gold particle or the like.

The process underlying the emission of photons by the particle being subjected to the light may be fluorescence. However, many other processes may also be used as a basis for the emission of photons, e.g. scattering of the light.

The respective process causing the emission of photons may be related to the properties of the particle to be tracked itself or to a marker, particularly a dye, marking the particle to be tracked.

In the method according to the present disclosure, the light intensity distribution applied to the sample features a spatially limited minimum. Like in case of the fluorescence inhibiting light used in STED or RESOLFT fluorescence microscopy, this intensity distribution may be formed by an interference pattern of one or more coherent light beams, in which the spatially limited minimum is a point of essentially zero intensity of the interference pattern. Thus, the minimum can be provided with small spatial dimensions. In particular, the spatial dimensions of the minimum may be smaller than the diffraction limit.

In contrast to STED and RESOLFT fluorescence microscopy, however, the light displaying this particular intensity distribution is not used for inhibiting fluorescence. Instead, it is used for driving the tracked particle for emission of photons to be detected as a measurement signal. Further, the sample is not scanned with the minimum of the intensity distribution, but the intensity distribution is continuously only moved with respect to the sample such that a rate of the photons emitted by the particle and subsequently detected is minimized. A minimized or minimal rate of the photons means that the particle is still located at the position of the minimum of the light intensity distribution. Vice versa, an increasing rate of the photons means that the particle tends to leave the minimum of the light intensity distribution; and that the position of the minimum has to be readjusted to track the movement of the particle.

In the method of the present disclosure, the photons or positions of their detection are not used for determining the actual position of the particle in the sample. Thus, there is no need to obtain a high number of photons for each position of the particle in the sample to determine the respective position at a high precision. Instead the actual position of the minimum of the light intensity distribution in the sample is taken as the actual position of the particle in the sample.

Under suitable conditions, the movement of the particle can be tracked at a spatial precision which is significantly below the diffraction limit. Besides small dimensions of the minimum and a high precision in moving the light intensity distribution, these suitable conditions include a sufficiently steep increase of the intensity of the light outside of the minimum, and a sufficiently fast readjustment of the position of the minimum in response to an increasing rate of the photons.

As it is not required that the particle emits many photons in the method according to the present disclosure, the risk of bleaching the particle is strongly reduced. Hence, even particles which are prone to bleaching can be tracked for longer periods of time or over longer distances covered by the particle in the sample. Further, in contrast to methods based on STED or RESOLFT fluorescence microscopy, the sample is only subjected to the intensity distribution comprising the minimum. Thus, the light needs not to be aligned to another beam of light, neither spatially nor with regard to its wavelength. Because of this, an optical setup for applying the method according to the present disclosure is significantly less complex than that of a STED or RESOLFT fluorescence microscope.

There is also another difference to STED and RESOLFT fluorescence microscopy: In the method according to the present disclosure the light intensity distribution with the minimum only needs to have a small absolute intensity, provided that the light already causes the emission of photons at low intensities. Especially, it is not required that a saturation of the excitation for emission of photons is achieved outside the zero point in order to achieve a spatial precision below the diffraction limit. Instead, in many cases, it is preferred that the excitation continuously increases with increasing distance to the zero point. Last but not least, it is a feature of the disclosure that the number of photons emitted by the tracked particle is minimized and thus the risk of its bleaching is also minimized.

Moving or deflecting the intensity distribution relative, i.e. with regard to the sample for continuously minimizing the rate of the photons detected by a detector may be based on a trial and error approach. I.e. the intensity distribution is moved on a trial basis in small steps. If the movement causes a decrease of the rate of the detected photons resembling the rate of the emitted photons, the intensity distribution is further moved in the same direction. In the opposite case, i. e. if the movement causes an increase of the rate of the detected photons, the intensity distribution is moved into another direction, e.g. the opposite direction. Various suitable algorithms and embodiments, like those indicated by the keywords "tracking-algorithm" and "fuzzy-logic", are known to those skilled in the art.

From STED or RESOLFT fluorescence microscopy various techniques are known for forming a light intensity distribution of fluorescence inhibiting light comprising a minimum, see, for example, Klar et al., PNAS 97 (2000), Westphal et al., Phys. Rev. Lett. 94 (2005) and Donnert et al., PNAS 103 (2003) whose disclosures are incorporated herein by reference in their entirety. Any of these techniques may also be used in the method according to the present disclosure for forming the light intensity distribution of the light driving the tracked particle to emit photons. To give only some examples, phase filters, spatial light modulators, 4 pi arrangements using opposing lenses, and the like may employed for forming the light intensity distribution comprising the minimum.

For moving or deflecting the light intensity distribution with the minimum with respect to the sample, a scanner may be applied as also known from STED and RESOLFT fluorescence microscopy. For example, such a scanner comprises acousto-optic or electro-optic deflectors, rotating mirrors, piezo-electric actuators by which the sample is adjusted with respect to the light beams, or piezo-electric actuators which actuate an objective lens and by which the light beams are adjusted with respect to the sample.

Alternatively or additionally to deflecting the light intensity distribution, moving the light intensity distribution with the minimum with respect to the sample may also be accomplished by shifting the sample with regard to the light intensity distribution featuring the minimum. Moving the light intensity distribution with the minimum with respect to the sample only requires a relative movement between the light intensity distribution with the minimum and the sample. Particularly, moving the light intensity distribution with the minimum with respect to the sample in x- and y-directions may be achieved by deflecting the light intensity distribution, and moving the light intensity distribution with the minimum with respect to the sample in z-direction may be achieved by shifting the sample. The z-direction may be the direction orthogonal to the plane of main extension of the surface of the sample via which the light intensity distribution is applied to the sample, and the x- and y-directions may extend along or in parallel to this plane of main extension.

According to the method of the present disclosure, the minimum of the light intensity distribution may be spatially limited in one, two or three dimensions, i.e. the minimum may extend along a plane, along a line or around a point. For tracking the movement of the particle, the intensity distribution is then moved or deflected with respect to the sample in all directions of that dimensions in which the minimum is limited. A movement in a direction in which the minimum is not limited will not cause a reduction of the rate of photons emitted by the particle and may thus not be used effectively. This also means that a movement of the particle in this direction cannot be tracked. Consequently, this direction is preferably oriented such that a movement of the particle in this direction is not expected. In many cases movements of particles in a sample are anyway confined to a direction along a particular structure. In case of a two-dimensional sample, the movement of the particle in the direction of the third dimension is omitted as a matter of principle.

It has already been mentioned that the intensity distribution with the minimum may be formed as an interference pattern of one or more coherent partial light beams, in which the spatially limited minimum is a point of essentially zero intensity. The interference pattern may, for example, be formed from one coherent beam by modulating its wavefronts, or from a plurality of superimposed coherent light beams.

In one embodiment of the method of the present disclosure, the modulation of the wavefronts of one coherent light beam is dynamically varied such that an only one- or two-dimensionally limited minimum of the light intensity distribution is alternately spatially limited in different spatial dimensions. For example, the phase relation may be varied between a first and a second phase relation such that the minimum is limited by a ring in a x-y-plane in case of the first phase relation, and such that the minimum is limited in z-direction in case of the second phase relation. Suitable light intensity distributions for limiting a minimum either in x- and y-direction or in z-direction, and the corresponding modulations of the wavefronts of a coherent light beam are described in J. Keller at al.: "Efficient fluorescence inhibition patterns for RESOLFT microscopy", Optics Express 3361, Vol. 15, No. 6 (2007), and also B. HArke et al., NanoLetters, 8, 1309 (2008), whose disclosures are incorporated herein by reference in its entireties. J. Keller et al. and B. Harke et al. use their patterns for fluorescence inhibition. The same patterns, however, may be used in the method of the present disclosure for the light intensity distribution of the light driving the particle to emit photons. In another variant of this embodiment of the present disclosure, different, successive phase relations may result in line- or plane-like minima which are oriented in different directions. These minima may be described as rotating stripes and comprise a point or a line as their spatial intersection. If one switches fast between such phase relations and if the minimum of the rate of the photons emitted by the particle is located either individually for each phase relation or over the whole variation of the phase relations, the movement of the particle in the sample may be tracked in all three dimensions.

In the method of the present disclosure, the light may consist of light components of different wavelengths. Further, the light may be of variable wavelengths to be able to track different particles belonging to different groups of particles. In all these cases it is an advantage if the light intensity distribution is formed in such a way that the spatial position of its spatially limited minimum does not vary with the wavelength of the light.

In the method of the present disclosure, the photons emitted by the particle need not to be detected by a two-dimensional detector array. Instead it is sufficient to use a point detector for detecting the photons since the tracking primarily depends on the rate of these photons. The current position of the particle in the sample will be determined from the current position of the intensity distribution with the minimum relative to the sample. This position may be concluded from the positions of those devices by which the intensity distribution is moved with respect to the sample, e.g. by the current position of the scanner used for moving the intensity distribution. The position of the intensity distribution relative to the sample may also be directly determined, by, for example, detecting the photons emitted by the particle with a camera imaging the sample and by evaluating an image of the light intensity distribution consisting of these photons on the camera. According to the principles of localization, this determination also allows for achieving a position precision beyond the diffraction limit.

Further, a camera imaging the sample may be used to determine an initial position of the particle by illuminating the sample with light driving the particles to emit photons, without spatially structuring the light. In case that two or more particles are determined which emit photons and cannot be tracked separately from each other, it is possible to photochemically bleach the surplus particles by purposefully applying high light intensities as they are, for example, present in maxima of the light intensity distribution adjacent to its minimum. Such a bleaching of perturbing particles may also be applied if an increasing rate of the detected photons is not due to the tracked particle having moved but due to another particle of a similar kind crossing the path of the tracked particle. This other particle may, for example via the camera, be recognized by a higher number of photons emitted further away from the minimum of the intensity distribution of the light.

A camera imaging the sample may also be used to determine a direction of the movement of the particle from the positions where the photons emitted by the particle are detected with the camera. For this determination it is also possible that a localization of the particles is performed, wherein the localization is based on the photons emitted by the particle when leaving the minimum of the intensity distribution of the light. Here, however, it is not required that the localization is performed with high precision. Thus, it is not required that the particle emits many photons since the emitted photons are only used for determining a direction in which the minimum of the intensity distribution of the light has to be moved to follow the particle. However, the emitted photons are not needed for achieving the desired spatial precision in tracking the particle. Instead, the spatial precision is achieved by the subsequent minimizing of the rate of the photons emitted by the particle and thus by the form and/or the arrangement of the minimum of the light intensity distribution. This minimizing may also be based on a trial and error procedure for readjusting the spatially limited minimum of the light intensity distribution.

It is not necessary, however, to use a full camera for determining a direction of the movement of the particle based on the positions where the photons emitted by the particle are detected. Sufficient information for such a determination is also available when using at least two adjacent point detectors for tracking the particle in one dimension or at least three adjacent point detectors for tracking the particle in two or three dimensions. A similar concept is used in known four-quadrant photo diodes for determining the position of a laser beam, for example. Further, S. J. Sahl et al.: Fast molecular tracking maps nanoscale dynamics of plasma membrane lipids, PNAS, Apr. 13, 2010, Vol. 107, No. 15, 6829-6834, whose disclosure is incorporated herein by reference in its entirety, disclose the use of three adjacent point detectors provided by three fibre input faces for tracking a fluorescent particle in a standard molecular tracking procedure. These point detectors may also be used in the method of the present disclosure for detecting the photons emitted by the particle.

Since the method according to the present disclosure aims at a minimization of the rate of the photons emitted by the particle, the background which is detected in addition to those photons of interest gains importance. The background may for example be due to the light which is applied to the sample in order to drive the particles to emit photons and scattered to the detector, or due to autofluorescence of the sample. In order to minimize the influence of the background the light driving the particles to emit photons may be applied to the sample in pulses and the photons emitted by the particles may be detected in a limited time interval after each of the pulses of the light. This time interval or gate can be adjusted such that a maximal signal-to-noise ratio is achieved. Another approach for reducing the background is selecting the particle such that it is driven to emit photons by the light via a multiphoton process. Then, the photons emitted by the particle have a much shorter wavelength than the light which is applied to the sample, and the background due to this light can be easily suppressed by wavelength. Moreover, multiphoton excitation or absorption is confined to a region surrounding the particle in all three dimensions. Multiphoton excitation does not extend over an enlarged volume of the sample, thus minimizing unwanted (auto)fluorescence excitation. This confinement of multiphoton excitation is well known from multiphoton excitation fluorescence microscopy.

In the method of the present disclosure, the light for driving the particle to emit photons can be selected by wavelength from white light. By varying this selection, different particles belonging to different groups of particles can be tracked. Light sources providing white light are generally known. They are, for example, available from NKT Photonics, Denmark. These light sources provide light pulses of an essentially constant intensity over an extended range of wavelengths. The light used in the method of the present disclosure may be selected from this range.

In one embodiment of the method according to the present disclosure, the photons emitted by the tracked particle are additionally analyzed for determining at least one feature selected from the group of features consisting of wavelength, polarisation, absolute rate, relative numbers detected by adjacent point detectors, coincidence, and point in time after each pulse of the light. This allows for gathering additional information on or details of the particle tracked. These details may vary over the track of the particle. The resulting variations in the wavelength of the photons and the point in time of the photons after each pulse of the light can be analyzed to monitor these details. Particularly, a similar technique as described in A. Schönle and S. W. Hell: Fluorescence nanoscopy goes multicolor, Nature Biotechnology, Vol. 25, No. 11, November 2007, 1243-1235, whose disclosure is incorporated herein by reference in its entirety, can be applied. The analysis of the details of particle in this way is highly sensitive. This is due to the fact that only a single particle contributes the photons analysed, i. e. there is no dilution by photons from other particles with other details. This particularly allows for an exact classification of the tracked particle based on subtle differences of the wavelength or other characteristics of the photons emitted by the particle.

Analyzing the photons coming from the particle also allows for determining whether the particle comprises one or more light emitting centers, and whether theses light emitting centers are staying together or depart from another at some time. Thus, for example, bonds and complexes can be monitored with regard to their individual binding partners or complex partners, respectively.

In the method of the present disclosure, a detector used for detecting the photons emitted by the particle will also detect all photons emitted by other particles belonging to the same group of particles and also located in the detection volume of the detector. The method of the present disclosure, however, will only work properly, if a single particle emits all the photons detected and considered in the rate of the photons minimized for tracking the particle. To confirm that this condition is met, the photons emitted out of the detection volume of the detector, i. e. out of a volume including the minimum of the light intensity distribution, can be analyzed for determining one or more of the above mentioned features, and the determined features can be checked for compliance with a single particle emitting the analysed photons. Particularly in this context, the feature of the absolute rate of the photons emitted by the particle, may also be called brightness of the particle. If the photons are emitted by more than one particle, all but one particle should be switched-off or bleached, or another particle should be selected in another part of the sample.

The method according to the present disclosure may be applied to track a switchable particle, for example a switchable molecule, wherein the light for driving the emission of photons may cause an activation of the switchable molecule from a state in which the particle cannot be driven to emit photons into a fluorescence state in which the particle can be driven to emit photons. One example for such a switchable molecule is called PADRON which is a Green Fluorescent Protein (GFP)-like protein. Although not required, it may be preferred in this embodiment that the particle quickly returns into the non fluorescent dark state, since this supports the effect of minimizing the rate of the emitted photons achieved in the minimum of the intensity distribution of the light driving the emission of photons. The return of the particle into the dark state may occur spontaneously or may be induced by any physical or chemical signal. Since is not required that this inducing signal is spatially structured, it is preferably not spatially structured.

In another embodiment of the present disclosure using switchable particles, light of another wavelength than that of the light driving the emission of photons may, for example, be used for adjusting a small concentration of activated particles which can be driven to emit photons in the sample as it is required for any tracking of single particles. For this purpose, the photoswitchable proteins called DRONPA, rsEGFP, EOS and Dendra2 may be used, which are activated at another wavelength than their excitation wavelength. DRONPA and rsEGFP are not only excited for emitting photons but also deactivated at their excitation wavelength. Due to the low number of photons needed for the method of the present disclosure, they may nevertheless be successfully tracked over some time with the light intensity distribution of excitation light. EOS and Dendra2 are not deactivated in the first place at their excitation wavelength; they may only bleach.

In all embodiments of the present disclosure using switchable particles, the light for driving the emission of photons, which is formed to provide the light intensity distribution with the spatially limited minimum, may either only comprise one light component of one wavelength or two components of different wavelengths. In case of only one light component, the light component may either excite the particles for the emission of photons which have already been switched-on or activated in another way, or it both activates and excites the particles for the emission of the photons. In case of two light components, one of these two light components may be used to activate the particles, whereas the other one of the light components excites them for the emission of the photons.

In one embodiment of the present disclosure, a separate switch-off signal is provided with a signal intensity distribution and enclosing the light intensity distribution. This switch-off signal switches off other particles belonging to the group of particles which are driven to emit photons when subjected to the light. Switching off may take place by photochemically bleaching or by switching a photo-deactivatable particles in a stable dark state, for example. This embodiment of the disclosure ensures that particles crossing the path of the tracked particle do not disturb its tracking by emitting photons contributing to the rate of photons to be minimized. The switch-off signal may be switch-off light. The switch-off signal may generally be formed in the same way as the light and concentrically with respect to the minimum of the intensity distribution of the light but with a larger minimum of the switch-off signal in the common centre. This larger minimum of the switch-off signal avoids that the tracked particle is switched off.

In one embodiment of the method of the present disclosure, the photons emitted by the particle and detected are counted, and an absolute number of the photons, that have already been emitted by the particle and detected, is indicated. Each particle may typically be driven to emit a number of photons before the particle is bleached and thus no longer trackable. This number of photons is not absolutely fix but does not vary strongly within each group of particles. Thus the absolute number of the photons, that have already been emitted by the particle and detected, is a good indicator of that part of the trackable lifetime of the particle which has already expired and of a remainder of the trackable lifetime over which the particle may still be tracked.

In one embodiment of the method of the present disclosure, at least two particles selected from the same group of particles which are driven to emit photons when subjected to the light, are alternately tracked by the minimum of the light intensity distribution. Those scanners already mentioned above which are known from STED and RESOLFT fluorescent microscopy are suitable to reposition the minimum of the light intensity distribution at a high accuracy much quicker than any particle may move in the sample. Other suitable scanners are those which are already used for tracking and trapping multiple particles, like, for example, in optical tweezers. Thus, a plurality of particles may be tracked in parallel in that the steps of the method according to the present disclosure are alternately executed with regard to each of the plurality of particles.

In a variant of the embodiment of the present disclosure described in the preceding paragraph, the light intensity distribution is periodically moved forth an back along a line or trajectory through the sample, on which two or more particles selected from the same group of particles are located. In all directions perpendicular to this line or trajectory, the two or more particles are directly tracked in that the course of this line is readjusted to minimize the rate of the photons emitted by the particles. The positions of the particles along the line, however, can be determined from the positions of local minima of the rate of the detected photons emitted by the particles along the line. This embodiment also allows for separately tracking particles which are very close to each other. In this case, the line along which the light intensity distribution is moved forth and back may particularly extend in the direction of the distance between the particles. In this embodiment, the distance of the particles is the distance of the local minima of the rate of the detected photons along the line.

It is also possible to track movements of two or more different particles according to the method of the present disclosure. For this purpose, light of two or more different wavelengths or polarizations may be used, and photons of wavelengths or polarizations being characteristic for the respective particles may be detected. Apart from a common objective lens, this tracking of two or more different particles may be performed with separate devices. In another embodiment of the present disclosure, there are separate light sources only, whereas all other parts of the tracking setup are shared. All shared parts will be used in an alternating manner for both particles, i.e. by switching between the tracking of the one particle and the tracking of the other particle.

The method of the present disclosure may also be used for imaging the sample. For this purpose, a dwell time of the particle may be determined for each of a plurality of parts of the sample. These parts of the sample may particularly be volume elements or voxels into which the entire volume of the sample is subdivided. When a distribution of the dwell times over the sample is mapped, an image of the sample is obtained. In a basic embodiment, the resulting image of the sample may indicate all areas of the sample in which the tracked particle has been or all areas in which the tracked particle has not been. A more refined image may indicate different areas of different dwell times. For example, an area in which the particle has rarely been is mapped separately from an area in which the particle has been often. From these different dwell times of the particle in the respective areas one may conclude that these areas of the sample are different themselves. They will particularly differ in accessibility to the particle or mobility of the particle or affinity to the particle or even a tendency to bind the particle.

One may additionally differ between an absolute dwell time of the particle calculated as the sum of all individual dwell times of the particle in the respective part of the sample, for example, and a temporary dwell time calculated as an average value of the individual dwell times of the particle in the respective part of the sample, for example. The absolute dwell time may be more indicative on affinity of the respective part of the sample to the particle, whereas the temporary dwell time may be more indicative on mobility of the particle in the respective part of the sample.

It should be understood that this way of imaging the sample does not only allow to obtain one fixed image of the sample. Instead, a temporal development of the dwell times in the different parts of the sample may also be used to obtain a sequence of images, i.e. a movie indicative of a temporal development of the sample.

The spatial resolution of this way of imaging the sample depends on the size of the voxels for which the dwell times are determined. As the position of the particle in the sample can be tracked at a precision beyond the diffraction barrier, the image may also have a spatial resolution beyond the diffraction barrier.

If the particle has been tracked over a long way in the sample, this may be sufficient to image the entire sample. If the mapping of dwell times is, however, repeated for each of a plurality of particles, different areas of the sample can be recognized which are separated by partitions through which the particles can not pass or may only pass at a low rate.

If different particles which are driven to emit photons when subjected to light of different compositions are used in this embodiment of the present disclosure, a multi-colour image of the sample is obtained. Each "colour" of this image is associated with a different property of the sample, for which the particles of the respective group of particles serve as a probe.

An apparatus according to the present disclosure comprises a light source providing the light which is used for driving the particle to emit photons, and a detector for detecting the photons emitted by the particle. The apparatus further comprises beam shaping means configured to apply the light with an intensity distribution featuring a spatially limited minimum to the sample. Further, beam deflecting means are provided which are controlled depending on a signal of the detector. The actual dependence is such that a rate of the photons detected by the detector is kept minimal by moving or deflecting the light intensity distribution with respect to the sample. Thus, the moving particle is tracked with the minimum of the light intensity distribution.

In one embodiment of the present disclosure, the beam shaping means modulate wavefronts of a coherent beam of the light, and then focus the beam into the sample to provide the minimum of the light intensity distribution as a point of essentially zero intensity of an interference pattern of the light. For modulating the wavefronts of the light beam the beam shaping means may comprise a dynamically controllable spatial light modulator.

In another embodiment of the present disclosure, the beam shaping means focus at least two coherent beams of the light into a same focal region in the sample. Also in this case, they provide the minimum of the light intensity distribution as a point of essentially zero intensity of an interference pattern Further, the beam shaping means may be achromatic, such that the spatial position of the spatially limited minimum does not vary with a wavelength of the light.

A camera may be provided for imaging the sample. The camera may, for example, be used to determine where a particle to be tracked is located in the sample. For this determination, the sample may be subjected to the light without spatial structure. The camera may also be used to determine the position of the light intensity distribution when the particle is tracked in the sample. Moreover, the camera may be used to determine the direction in which the intensity distribution has to be moved for tracking the particle. Instead of a camera, one or preferably two or more adjacent point detectors may be provided for determining the direction in which the intensity distribution starts to move for tracking the particle. Particularly, a set of multimode optical fibres as described in S. J. Sahl et al.: Fast molecular tracking maps nanoscale dynamics of plasma membrane lipids, PNAS, Apr. 13, 2010, Vol. 107, No. 15, 6829-6834, may be used as adjacent point detectors.

For tracking two different particles, two light sources providing light of different wavelengths may be provided. For a simultaneous tracking, separate beam shaping means and beam deflecting means may be provided for each of the light sources. However, it is also possible that common means are provided for both light sources which are used in an alternating manner. It is also possible that more than two light sources are provided for a simultaneous or fast alternating tracking of more than two particles.

Particularly, the light source may be a pulsed light source like a pulsed laser such that the light is applied to the sample in pulses. The detector may then be provided with a gate and synchronized with the pulsed light source such that the photons emitted by the particle are detected after each pulse of the light in a limited time interval at a maximum signal-to-noise ratio. This procedure is also known as time-gated detection.

In one embodiment of the apparatus according to the present disclosure, the light source comprises a selector configured to select the light from white light by, for example wavelength or polarisation. The white light may then particularly be provided by some known pulsed light source as available from NKT Photonics, Denmark, for example.

The detector of the apparatus according to the present disclosure may further comprise an analyzer configured to analyze the photons emitted out of the volume including the minimum of the light intensity distribution for at least one feature selected from the group of features consisting of wavelength, polarisation, absolute rate, relative numbers detected by adjacent point detectors, coincidence, and detection time point after each pulse of the light. The analyzer allows for gathering information about permanent and changing details of the particle. Based on this information the particle may be identified or assigned to a particular class of particle. The analyzer also allows for determining whether the photons are emitted by just one or more particles which may be associated.

The detector of the apparatus according to the present disclosure may further detect the photons emitted by the particle selectively at a wavelength which is essentially half of a wavelength of the light provided by the light source. This means that the particle is driven to emit the photons via a two photon process. Due to the high difference in wavelength between the light driving the particle to emit photons and the photons emitted by the particle, suppressing a background in detecting the photons becomes particularly easy. Further, in case of a two photon process driving the particle to emit photons, the probability that the light erroneously also drives particles to emit photons in other areas of the sample is strongly reduced. This particularly applies to particles at other positions in z-direction than the focal plane into which the light is focused, with z denoting the optical axis along which the light is focused. Multiphoton induced processes primarily occur at the focal region of highest intensity, thus confining excitation in all three dimensions.

The same z-selective property of multiphoton processes may also be used in, via a multiphoton process, selectively activating an activatable particle at a certain z-position in the sample by activation light focused to a focal region at that z-position. i.e. at that depth in the direction of the optical axis.

Further, the apparatus of the present disclosure may comprise a signal source providing a switch-off signal, particularly switch-off light, with a signal intensity distribution enclosing the light intensity distribution. If the switch-off signal switches-off other particles emitting photons when subjected to the light, these other particles are already switched-off before they will be subjected to the light due to a movement of the light intensity distribution or the other particles. Thus, the other particles will not emit photons which might disturb the tracking of the particle. The switch-off signal may, for example, deactivate an active particle into a deactivated state in which it can no longer be driven for the emission of photons. In another embodiment, the switch-off signal, by stimulated emission, prohibits the occupation of an excited molecular state out of which the particles emits the detected photons. In this way, the effective point spread function indicating the area of the sample in which the particle is effectively driven for the emission of photons by the combined intensity distributions of the light and the switch-off signal is spatially limited to a small region enclosing the minimum of the light intensity distribution.

The apparatus according to the present disclosure may comprise a counter counting the photons emitted out of the volume including the minimum of the light intensity distribution and detected by the detector, and to indicate an absolute number of the counted photons. The indication of the absolute number of the counted photons may be a relative indication indicating a percentage of the photons already counted for one particle with regard to an expected number of photons that may be expected to be emitted by the particle, before it is bleached.

The apparatus according to the present disclosure may comprise at least one further light source to provide further light for driving a further particle to emit photons. The further light may differ from the light in wavelengths or polarization of at least one of its light components. The light source and the at least one further light source may be configured to simultaneously or alternately track movements of the particle and the further particle.

Even with only one light source, the apparatus according to the present disclosure may be used to track a number of particles in parallel, i.e. essentially at the same time. This may, for example, be achieved in that the beam deflecting means are configured to alternately track the particle and at least one other particle with the minimum of the light intensity distribution. If the beam deflecting means, for example, comprise an acousto-optical deflector or a fast electro-optical deflector, the spatially limited minimum of the light intensity distribution can be alternately adjusted to two or even more particles much quicker than any possible movement of the particles.

As already pointed out before, the minimum of the light intensity distribution can be translated at high speed along a line or trajectory such that the detected time-dependence measurement signal, i.e. the rate of the detected photons, features minima as a function of time or position along the trajectory. Each minimum represents one particle. The position of the respective particle can be determined from the location of the respective minimum of the measurement signal, either directly or after mathematical evaluation. Mathematical evaluation may include linear or non-linear deconvolution with the mathematical response to a single particle. Thus, multiple particles may be tracked at high speed and with a high spatial resolution.

Since an apparatus according to the present disclosure only needs to provide light for driving the particle for emission, its setup may be kept simple. However, the apparatus according to the present disclosure may also be realized on a basis of or as a combination with an (potentially already existing) STED or RESOLFT fluorescence microscope. Particularly, the beam shaping means which are used for that light inhibiting fluorescence in a STED or RESOLFT fluorescence microscope may be used for the light by which the particle is driven to emit photons in the present disclosure. Further, the beam deflecting means used for scanning the sample may be easily adapted to be used for a tracking of the particle by minimizing the rate of detected photons. When implementing the present disclosure on a STED or RESOLFT fluorescence microscope, there is the option to additionally image the sample by STED or RESOLFT fluorescence microscopy at any time like, for example, prior to or after executing the method of the present disclosure or even at some time in between.

Referring now in greater detail to the drawings, FIG. 1 shows an apparatus 1 for tracking the movement of a particle 2 in a sample 3. The particle 2 may, for example, be a fluorescent marker, or the particle 2 may be marked with such a fluorescent marker. By light 4 from a light source 5 the fluorescent marker is driven to emit photons. This essentially only occurs outside of a minimum of an intensity distribution of the light 4 in the sample 3. This intensity distribution is described in more detail with reference to FIGS. 3 to 6. The light source 5 comprises a laser 6. Beam shaping means 7 are provided for forming the desired light intensity distribution in the focal volume of an objective lens 8; and beam deflecting means 9, 10 and 11 are provided for adjusting the position of the minimum of the intensity distribution of the light 4 in the sample 3. The beam deflecting means 9 and 10 directly work on the light 4 and move or deflect the minimum in x- and/or y-direction, i.e. in lateral direction with regard to the light path. The beam deflecting means 11, however, directly work on the sample 3 and move or deflect the minimum of the intensity distribution of the light 4 with respect to the sample 3 in z-direction. Behind a dichroic beam splitter 13, a point detector 12 is provided for selectively detecting photons emitted by the particle 2. The beam splitter 13 is located in the optical path between the laser 6 and the sample 3, and in particular between the laser 6 and the beam deflecting means 9 and 10. Another beam splitter 14 is located between the beam deflecting means 9 and 10 and the objective lens 8. Via the beam splitter 14 a camera 15 including a two-dimensional detector monitors the sample 3. For initially locating the particle 2, the light 4 is applied to the sample 3 over a large area and the particle 2 is located on the basis of the photons emitted by the particle 2 and imaged with the camera 15. Then, the intensity distribution of the light 4 is adjusted with respect to the particle 2 such that the particle 2 is located at the position of the minimum of the intensity distribution of the light 4. That the particle 2 is indeed located at the position of the minimum is checked by moving the intensity distribution of the light 4 with respect to the sample 3 on a trial basis. Upon these movements the rate of the photons emitted by the particle 2 which are detected by the point detector 12 should increase. However, a decrease of the rate indicates that the intensity distribution of the light 4 has to be adjusted to track the particle 2 with the minimum because the particle 2 has moved. An increase of the rate of the photons without movement of the intensity distribution of the light 4 also means that the particle 2 has moved in the sample 3. Then, the intensity distribution of the light 4 has to be moved in order to track the particle 2 with the minimum until the rate of the photons has reached its minimum again. For this tracking, the beam deflection means 9 to 11 are controlled by a controller 16 in dependence on the signal of the detector 12. The position and/or movement of the minimum of the intensity distribution of the light 4 which is determined during the tracking resembles the movement of the particle 2 in the sample 3. A direction of the movement of the particle 2 may be determined from those positions where the photons emitted by the particle 2 are detected by the camera 15, i.e. where the particle gets out of the minimum, to support the tracking of the particle with the minimum.

In FIG. 1 it is indicated that the controller 16 also controls the beam shaping means 7. In practice, the beam shaping means 7 may be a spatial light modulator by which different intensity distributions of the light 4 in the sample 3 may be appropriately adjusted. The minima of these light intensity distributions are each limited in one or two dimensions and only comprise a common point of intersection with which the particle 2 can be tracked in the sample 3. This embodiment enables to track the particle 2 with regard to its movement in the sample 3 with maximal spatial precision in all three dimensions.

Figure 2:
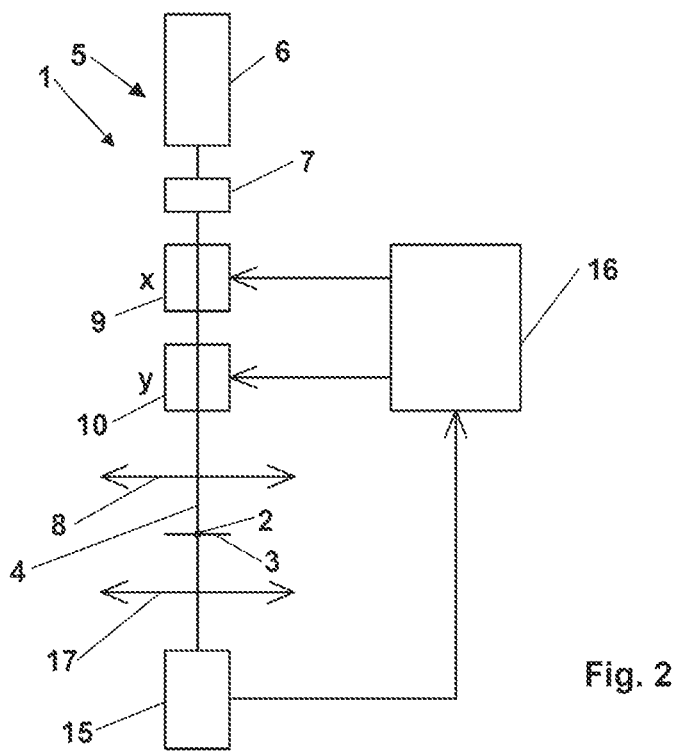
FIG. 2 shows another exemplary embodiment of the apparatus according to the present disclosure for performing another embodiment of the method according to the present disclosure, the apparatus comprising one light source and a camera.

The embodiment of the apparatus 1 illustrated in FIG. 2 does not comprise the point detector 12 according to FIG. 1. Here only the camera 15 is provided for detecting the photons emitted by the particle 2 in the sample 3. Further, the sample 3 is a sample essentially extending in two-dimensions only. The intensity distribution of the light 4 comprises a central minimum surrounded by a ring-like maximum with which the particle 2 is tracked. This doughnut-shaped intensity distribution of the light 4 is generated with the help of static beam shaping means 7. In the plane of the two-dimensional sample 3 the minimum of the intensity distribution of the light 4 is located with the beam deflecting means 9 and 10 which directly work on the light 4. The camera 15 is arranged behind a further objective lens 17 which is arranged on the side of the sample 3 opposite the objective lens 8. Here, the camera 15 is additionally used to determine the position of the intensity distribution of the light 4 in the sample 3. This allows to determine the current position of the beam deflecting means 9 and 10 on the one hand. On the other hand, this can be used to determine the position of the minimum of the intensity distribution of the light 4 in the sample. In particular, the position of the minimum in the sample may thus also be determined at a spatial precision beyond the diffraction limit.

In order to establish a direction of movement of the particle in the Z-direction of the optical axis, an additional optical means can be provided (not depicted here). Such a means is known from centroid-based single particle tracking and movement. The means, for example, makes use of astigmatism (see, for example, Huang et al., Science 319 (2008)) or of double-helical detection PSF (see, for example, Pavani et al., PNAS 106 (2009)). Astigmatism may, for example, be provided by inserting a cylindrical lens in the path of the photons emitted by the particle, i.e. somewhere between the sample and the detector or camera.

Figure 3:
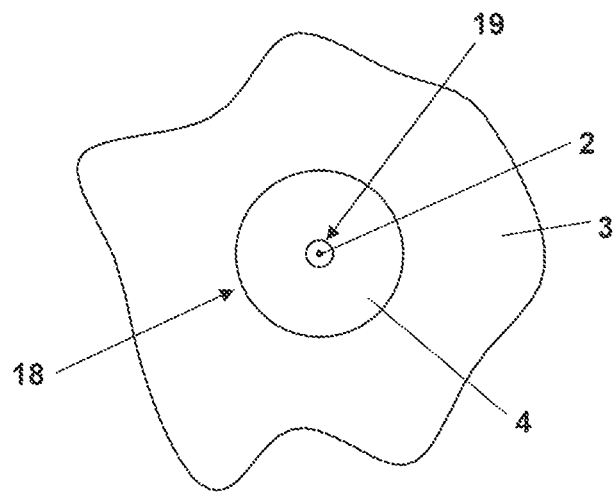
FIG. 3 shows a particle in a region of a minimum of an intensity distribution for driving the particle to emit photons.
Figure 4:
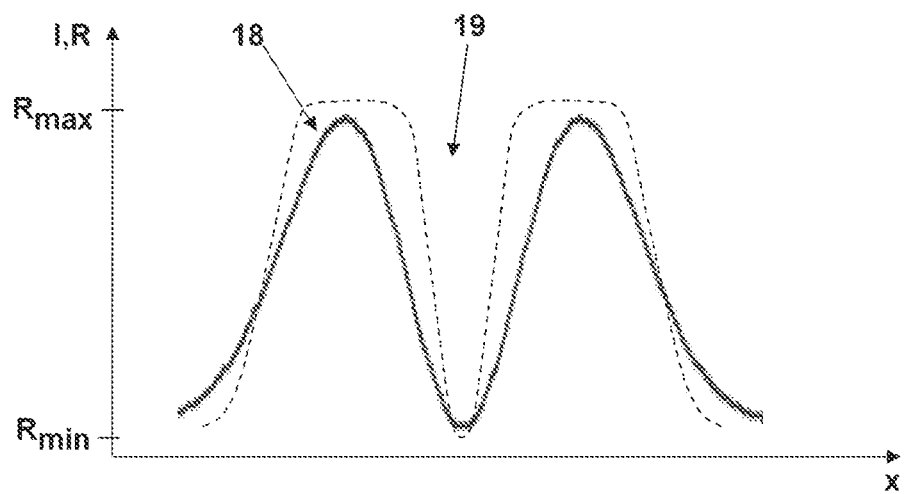
FIG. 4 shows the intensity of the intensity distribution according to FIG. 3 depending on the position along a line profile; further, the resulting rate of photons emitted by the particle according to FIG. 3 is shown.

FIG. 3 schematically shows the intensity distribution of the light 4 in the sample 3, the particle 2 being located at the central minimum 19 of the light intensity distribution 18. FIG. 4 is a graph showing the intensity I of the light intensity distribution 18 (straight line) along a line profile through the sample 3 according to FIG. 3 (at an increased scale). In the region of the minimum 19, the light intensity distribution 18 has an essentially sinusoidal curvature which is symmetric with regard to the minimum 19. In addition to the light intensity distribution 18, FIG. 3 shows the resulting rate R of the photons emitted by the particle 2 (dashed line) assuming that the particle 2 is subjected to the corresponding intensities I of the light 4. At the position of the minimum 19, the rate R also has its minimum value $R_{min}$. As soon as the particle 2 leaves this minimum 19, the rate R quickly increases. In particular, even at a small distance to the minimum 19 the rate R already reaches a value close to or equal to its maximum value $R_{max}$. This behaviour is advantageously used for tracking the particle 2 in the sample 3 with a minimum 19 of the light intensity distribution 18 at a high spatial precision.

Figure 5:
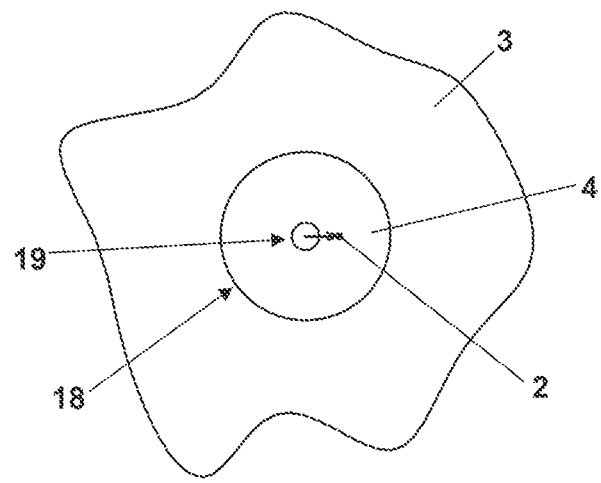
FIG. 5 shows the situation after a movement of the particle out of its position according to FIG. 3.
Figure 6:
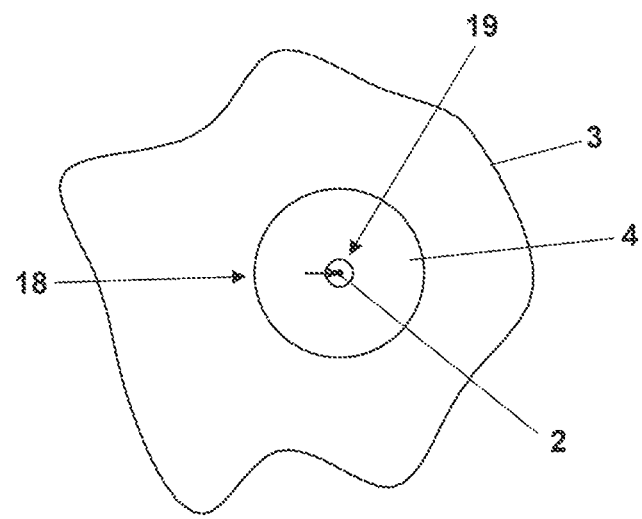
FIG. 6 shows the situation after the intensity distribution has followed the movement of the particle.

When the particle 2 has changed its position with respect to the intensity distribution 18 and has left the minimum 19 as illustrated in FIG. 5, an increased rate R of photons emitted by the particle 2 is detected. By moving the intensity distribution 18 in the sample 3 on a trial basis, the rate is reduced again and kept minimal. In this way, it is determined in which direction and by which distance the particle 2 has moved, since the minimum of the rate is not achieved before the light intensity distribution 18 with the minimum 19 has been moved in the same direction and by the same distance with respect to the sample 3 as illustrated in FIG. 6. The direction in which the intensity distribution 18 with the minimum 19 has to be moved to track the particle 2 may also be determined from the positions at which photons emitted by the particle 2 are detected with a camera.

Figure 7:
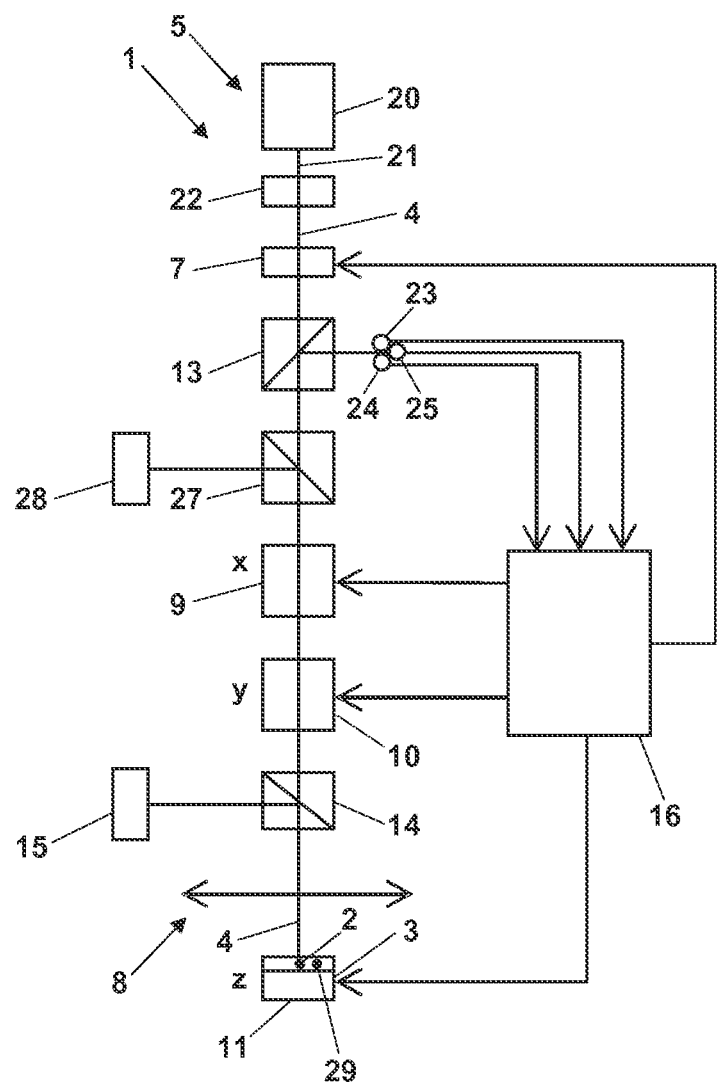
FIG. 7 shows a further exemplary embodiment of the apparatus according to the present disclosure for performing a further embodiment of the method according to the present disclosure, the apparatus comprising one light source including a source of white light and a selector, and three adjacent point detectors.

The embodiment of the apparatus 1 shown in FIG. 7 differs from that one shown in FIG. 1 by the following details. The light source 5 comprises a source 20 of white light 21 and a selector 22 selecting the light 4 from the white light 21 by wavelength. Further, instead of only one point detector 12 according to FIG. 1, three adjacent point detectors 23 to 25 provide the input to the controller 16. The relative numbers of the photons emitted by the particle 2 and detected by the point detectors 23 to 25 indicate the direction in which the particles 2 is moving within the sample 3. Further, the apparatus 1 of FIG. 7 comprises an additional beam splitter 27 and an analyzer 28 for the wavelength of the photons emitted by the particle 2. In this embodiment, the beam deflecting means 9 and 10 are configured to alternately track the movements of the particle 2 and a further particle 29 in the sample 3. This means that the spatially limited minimum of the light intensity distribution of the light 4 is alternately used to track the particle 2 and the particle 29, respectively.

Figure 8:
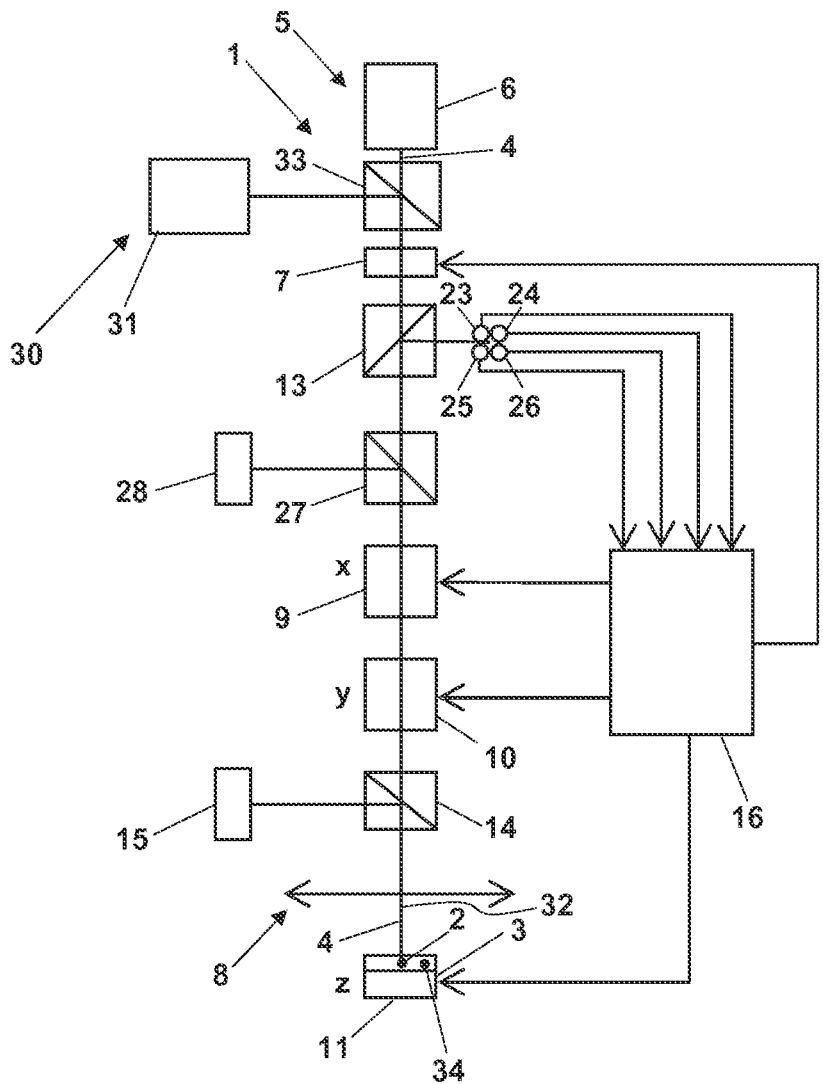
FIG. 8 shows an even further exemplary embodiment of the apparatus according to the present disclosure for performing an even further embodiment of the method according to the present disclosure, the apparatus comprising two light sources and four adjacent point detectors.

The embodiment of the apparatus 1 according to FIG. 8 is also based on the apparatus 1 according to FIG. 1 and is thus only described with regard to its differences here. The point detector 12 according to FIG. 1 is replaced by four adjacent point detectors 23 to 26. Besides the light source 5 comprising the laser 6 and providing the light 4, a further light source 30 comprising a further laser 31 providing further light 32 of another wavelength composition than the wavelength composition of the light 4. The further light 32 is combined with the light 4 via a dichroic beam splitter 33. The further light 32 is formed into a further light distribution by the beam shaping means 7 in a same way as the light 4. For this purpose, the beam shaping means 7 are achromatic. As both light sources 5 and 30 are pulsed, the photons emitted by the particle 2 in response to the light 4 and by a further different particle 34 in response to the light 32 can be separated timewise at the point detectors 23 to 26. The point detectors 23 to 26 may also be used to analyze the photons for a certain point in time after each pulse of the light 4 and 32, respectively. The apparatus 1 of FIG. 8 also comprises the same additional beam splitter 27 and analyzer 28 for the wavelength of the photons emitted by the particle 2 as the apparatus 1 of FIG. 7.

Figure 9:
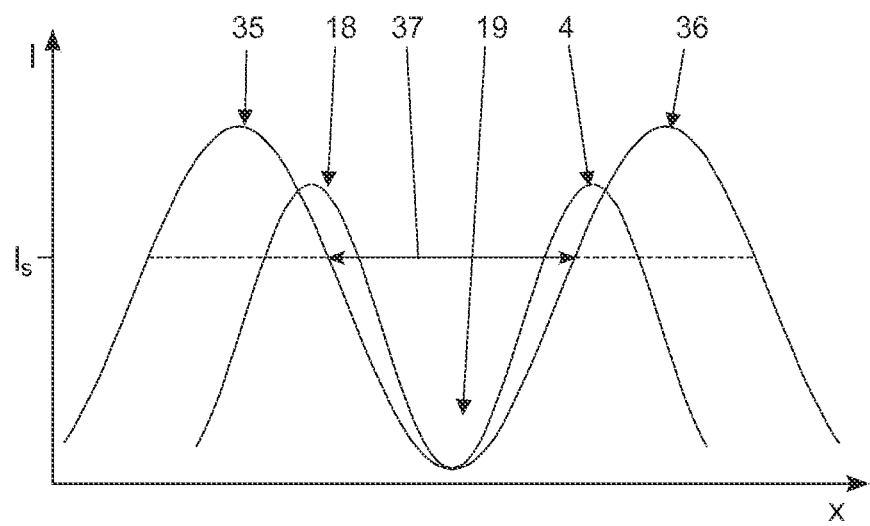
FIG. 9 shows a light intensity distribution and a switch-off signal intensity distribution enclosing the light intensity distribution in an x-section through the focal plane.

FIG. 9 shows a section in x-direction through a doughnut-shaped light intensity distribution 18 of light 4 driving or exciting a particle for the emission of photons. This light intensity distribution 18 is superimposed with an intensity distribution 35 of a switch-off signal preventing the emission of those photons which are detected in the method of the present disclosure. Particularly, the switch-off signal is STED light 36 prohibiting the occupation of an excited molecular state of the particle by stimulated emission. The intensity distributions 18 and 35 are concentric, i.e. they both display a minimum 19 at a common center. The distance of the maxima of the light intensity distribution 18 in x-direction, however, is somewhat smaller than a distance between the maxima of the intensity distribution 35 of the STED light 36 in x-direction. This corresponds to a longer wavelength of the STED light 36 as compared to the light 4. Further, the intensity distribution 35 exceeds a saturation intensity $I_S$ outside a region whose diameter is indicated by a double-headed arrow 37 in FIG. 9. Thus, only if located within this region, a particle is effectively driven to emit photons by the light 4, as the emission of photons which are detected is inhibited by the STED light 36 everywhere else.

Figure 10:
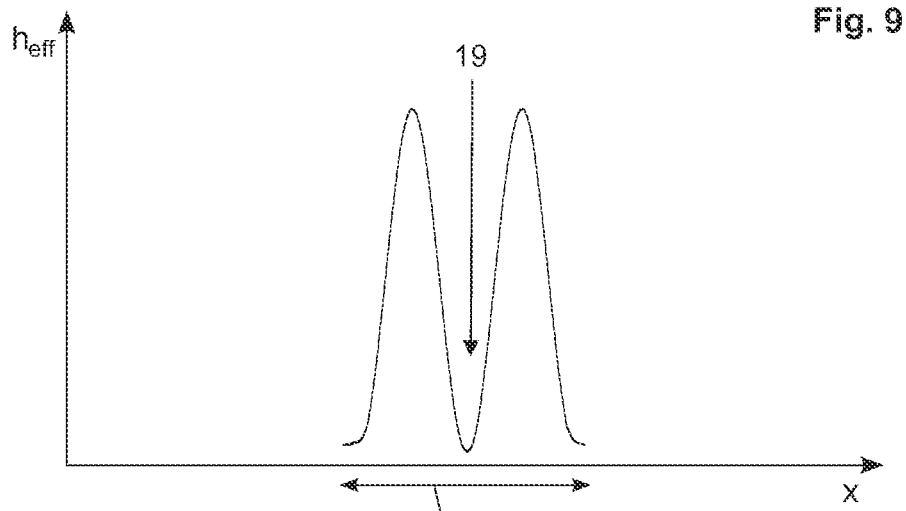
FIG. 10 shows an effective point spread function $h_{\mathit{eff}}$ resulting from the intensity distributions according to FIG. 9.

FIG. 10 shows the effective point spread function $h_{\text{eff}}$ resulting from the two superimposed light intensity distributions 18 and 35 of FIG. 9. A particle is only driven to emit photons if located within the region indicated by the double-headed arrow 37. As a result, a particle can be individually tracked by the method of the present disclosure as long as no other particle is located in the same narrow region. It is not necessary that the full volume covered by the light intensity distribution 18 according to FIG. 9 is free of other particles which would also be driven to emit photons by the light 4.

Many variations and modifications may be made to the embodiments of the disclosure without departing substantially from the spirit and principles of the disclosure. All such modifications and variations are intended to be included herein within the scope of the present disclosure, as defined by the following claims.

LIST OF REFERENCE NUMERALS 1 apparatus
2 particle
3 sample
4 light
5 light source
6 laser
7 beam shaping means
8 objective lens
9 beam deflecting means
10 beam deflecting means
11 beam deflecting means
12 point detector
13 beam splitter
14 beam splitter
15 camera
16 controller
17 objective lens
18 intensity distribution
19 minimum
20 source
21 white light
22 selector
23 point detector
24 point detector
25 point detector
26 point detector
27 beam splitter
28 analyzer
29 particle
30 light source
31 laser
32 light
33 beam splitter
34 particle
35 intensity distribution
36 STED light
37 arrow
I intensity
R rate

The invention claimed is:

1. A method of tracking a movement of a particle in a sample, the method comprising:
    providing light;
    selecting the particle from a group of particles which are driven to emit photons when subjected to the light;
    forming the light to provide a light intensity distribution comprising a spatially limited minimum;
    applying the light intensity distribution to the sample such that the particle is located in the spatially limited minimum of the light intensity distribution;
    detecting the photons emitted by the particle;
    tracking the movement of the particle with the spatially limited minimum of the light intensity distribution by
        moving the light intensity distribution with respect to the sample such that a rate of the photons emitted by the particle remains minimal, and
        taking an actual position of the spatially limited minimum of the light intensity distribution in the sample as an actual position of the particle in the sample.

2. The method of claim 1, wherein the spatially limited minimum of the light intensity distribution is spatially limited in at least one spatial dimension; and wherein the particle is tracked with the spatially limited minimum of the light intensity distribution in all directions of all dimensions in which the spatially limited minimum is spatially limited.

3. The method of claim 1, wherein the light is formed to provide the light intensity distribution in that wavefronts of a coherent beam of the light are modulated, and in that the beam of the light with the modulated wavefronts is focussed into the sample to provide the spatially limited minimum of the light intensity distribution as a point of essentially zero intensity of an interference pattern.

4. The method of claim 3, wherein a modulation of the wavefronts is dynamically varied such that the spatially limited minimum of the light intensity distribution is alternately spatially limited in different spatial dimensions.

5. The method of claim 1, wherein the light is formed to provide the light intensity distribution in that at least two coherent beams of the light are focussed into a same focal region in the sample to provide the spatially limited minimum of the light intensity distribution as a point of essentially zero intensity of an interference pattern.

6. The method of claim 1, wherein the light is formed to provide the light intensity distribution such that a spatial position of the spatially limited minimum does not vary with a wavelength of the light.

7. The method of claim 1, wherein the photons are detected by a point detector.

8. The method of claim 1, wherein the photons are detected by at least two adjacent point detectors.

9. The method of claims 8, wherein a direction of an initial movement of the particle is determined from relative numbers of photons emitted by the particle and detected by the adjacent point detectors.

10. The method of claim 1, wherein the sample is imaged with a camera.

11. The method of claim 10, wherein a starting position of the particle is determined with the camera when the sample is uniformly subjected to the light.

12. The method of claim 10, wherein the actual position of the spatially limited minimum of the light intensity distribution in the sample is determined on a basis of positions at which the light reflected by the sample is detected with the camera.

13. The method of claim 10, wherein a direction of an initial movement of the particle is determined on a basis of positions at which the photons emitted by the particle are detected by the camera.

14. The method of claim 1, wherein an actual position of the minimum spatially limited of the light intensity distribution in the sample is determined on a basis of actual settings of scanners used for moving the light intensity distribution with respect to the sample.

15. The method of claim 1, wherein the light is applied to the sample in pulses and wherein the photons emitted by the particle are detected in a limited time interval after each of the pulses.

16. The method of claim 15, wherein the light is selected from white light.

17. The method of claim 1, wherein the particle is selected from a group of particles which are driven to emit photons when subjected to the light by a multiphoton process.

18. The method of claim 1, wherein the photons emitted by the particle are analysed for determining at least one feature selected from a group of features consisting of
wavelength,
polarisation,
absolute rate,
relative numbers detected by adjacent point detectors,
coincidence, and
detection time point after each pulse of the light.

19. The method of claim 1, wherein photons emitted out of a detection volume including the spatially limited minimum of the light intensity distribution are analysed for determining at least one feature selected from a group of features consisting of
wavelength,
polarisation,
absolute rate,
relative numbers detected by adjacent point detectors,
coincidence, and
detection time point after each pulse of the light, and
wherein the determined at least one feature is checked for compliance with a single particle emitting the analysed photons.

20. The method of claim 1, wherein a number of particles in the sample, which belong to the group of particles, is reduced by bleaching at least one particle of the number of particles.

21. The method of claim 1, wherein the particle is selected from a subgroup of particles which are activatable from a first state in which the particles of the subgroup can not be driven to emit photons by the light into a second state in which the particles of the subgroup can be driven to emit photons by the light.

22. The method of claim 21, wherein the particle is selected from a sub-subgroup of particles which are activatable from the first state into the second state by activation light in a multiphoton process, and wherein the particle is activated by activation light focussed into the sample.

23. The method of claim 1, wherein a switch-off signal is provided with a signal intensity distribution enclosing the light intensity distribution, the switch-off signal switching-off other particles belonging to the group of particles which are driven to emit photons when subjected to the light.

24. The method of claim 1, wherein the photons emitted by the particle and detected are counted and wherein an absolute number of the photons, that have already been emitted by the particle and detected, is indicated.

25. The method of claim 1, wherein at least one further particle is selected from the group of particles which are driven to emit photons when subjected to the light; and wherein movements of the particle and of the at least one further particle are alternately tracked with the spatially limited minimum of the light intensity distribution.

26. The method of claim 1, wherein further light differing from the light in at least one light feature selected from wavelength and polarization of at least one light component is provided, wherein a further particle is selected from a further group of particles which are driven to emit photons when subjected to the further light; wherein the further light is formed to provide a further light intensity distribution comprising a further spatially limited minimum; wherein the further light intensity distribution is applied to the sample such that the further particle is located in the further spatially limited minimum of the further light intensity distribution; wherein the photons emitted by the further particle are detected; wherein the movement of the particle is tracked with the spatially limited minimum of the light intensity distribution by moving the further light intensity distribution with respect to the sample such that a rate of the photons emitted by the further particle remains minimal, and taking an actual position of the further minimum of the further light intensity distribution in the sample as an actual position of the further particle in the sample; and wherein the movements of the particle and the further particle are tracked simultaneously or alternately.

27. The method of claim 1, wherein, for each of a plurality of parts of the sample, a dwell time of the particle is determined, and wherein a distribution of the dwell times over the sample is mapped.

28. The method of claim 27, wherein all steps of the method are repeated for each of a plurality of particles, wherein the distributions of the dwell times of each of the plurality of particles are mapped separately.

29. A method of imaging a sample, the method comprising the steps of:
providing light of a first composition;
selecting a particle from a group of particles which are driven to emit photons when subjected to the light of the first composition;
forming the light of the first composition to provide a light intensity distribution comprising a spatially limited minimum;
applying the light intensity distribution to the sample such that the particle is located in the spatially limited minimum of the light intensity distribution;
detecting the photons emitted by the particle;
tracking a movement of the particle with the spatially limited minimum of the light intensity distribution by
moving the light intensity distribution with respect to the sample such that a rate of the photons emitted by the particle remains minimal, and
taking an actual position of the spatially limited minimum of the light intensity distribution in the sample as an actual position of the particle in the sample;
for each of a plurality of parts of the sample, determining a dwell time of the particle; and
mapping a distribution of the dwell times over the sample.

30. The method of claim 29, wherein the steps of tracking, determining and mapping are repeated for each of a plurality of particles selected from the group of particles.

31. The method of claim 29, comprising:
providing further light of a second composition differing from the first composition;
selecting a further particle from a further group of particles which are driven to emit photons when subjected to the further light;
forming the further light to provide a further light intensity distribution comprising a further spatially limited minimum;
applying the further light intensity distribution to the sample such that the further particle is located in the further spatially limited minimum of the further light intensity distribution:
detecting the photons emitted by the further particle;
tracking the movement of the further particle with the spatially limited minimum of the further light intensity distribution by
moving the further light intensity distribution with respect to the sample such that a rate of the photons emitted by the further particle remains minimal, and
taking an actual position of the further minimum of the further light intensity distribution in the sample as an actual position of the further particle in the sample;
for each of a plurality of parts of the sample, determining a further dwell time of the further particle; and
mapping a distribution of the further dwell times over the sample.

32. The method of claim 31, wherein steps of tracking, determining and mapping are repeated for each of a plurality of particles selected from the group of particles and for each of a plurality of further particles selected from the further group of particles.

33. An apparatus for tracking a movement of a particle in a sample, the apparatus comprising:
a light source configured to provide light for driving the particle to emit photons,
beam shaping means configured to apply the light to the sample with an intensity distribution comprising a spatially limited minimum,
a detector configured to detect photons emitted out of a volume including the spatially limited minimum of the light intensity distribution and to provide a signal indicating a rate of the photons detected, and
beam deflecting means configured to move the intensity distribution with respect to the sample in response to the signal of the detector such that the rate of the photons detected by the detector remains minimal.

34. The apparatus of claim 33, wherein the beam shaping means are configured to modulate wavefronts of a coherent beam of the light, and to focus the beam of the light with the modulated wavefronts into the sample to provide the spatially limited minimum of the light intensity distribution as a point of essentially zero intensity of an interference pattern.

35. The apparatus of claim 34, wherein the beam deflecting means are configured to alternately track the particle and at least one other particle with the spatially limited minimum of the light intensity distribution.

36. The apparatus of claim 33, wherein the beam shaping means comprise a dynamically controllable spatial light modulator.

37. The apparatus of claim 33, wherein the beam shaping means are configured to focus at least two coherent beams of the light into a same focal region in the sample to provide the spatially limited minimum of the light intensity distribution as a point of essentially zero intensity of an interference pattern.

38. The apparatus of claim 33, wherein the beam shaping means are achromatic.

39. The apparatus of claim 33, wherein the detector is a point detector.

40. The apparatus of claim 33, wherein the detector comprises two, three or four adjacent point detectors.

41. The apparatus of claim 33, wherein the detector is a camera.

42. The apparatus of claim 33, and further comprising a camera configured to image the sample.

43. The apparatus of claim 33, wherein the light source is a pulsed light source which applies the light to the sample in pulses and wherein the detector comprises a gate synchronized with the pulsed light source configured to detect the photons emitted by the particle in a limited time interval after each of the pulses.

44. The apparatus of claim 33, wherein the light source comprises a selector configured to select the light from white light.

45. The apparatus of claim 33 wherein the detector comprises an analyzer configured to analyse the photons emitted out of the volume including the spatially limited minimum of the light intensity distribution for at least one feature selected from a group of features consisting of
wavelength,
polarisation,
absolute rate,
relative numbers detected by adjacent point detectors,
coincidence, and
detection time point after each pulse of the light.

46. The apparatus of claim 33, wherein the detector detects the photons emitted out of the volume including the spatially limited minimum of the light intensity distribution selectively at a wavelength which is essentially half of a wavelength of the light provided by the light source.

47. The apparatus of claim 33, comprising a signal source configured to provide a switch-off signal with a signal intensity distribution enclosing the light intensity distribution, the switch-off signal switching-off other particles emitting photons when subjected to the light.

48. The apparatus of claim 33, comprising a counter configured to count the photons emitted out of the volume including the spatially limited minimum of the light intensity distribution and detected by the detector and to indicate an absolute number of the photons counted.

49. The apparatus of claim 33, comprising at least one further light source configured to provide further light for driving a further particle to emit photons, the further light differing from the light in at least one light feature selected from wavelength and polarization of at least one light component, wherein the light source and the at least one further light source are configured to simultaneously or alternately track movements of the particle and the further particle.

50. The apparatus of claim 33, wherein the beam deflecting means comprise at least one controllable beam deflector selected from acousto-optical deflectors and electro-optical deflectors.

* * * * *